United States Patent [19]

Mizutani et al.

[11] 4,411,891
[45] Oct. 25, 1983

[54] CATIONIZED DEXTRAN AND SALTS THEREOF AND MANUFACTURING PROCESS AND UTILIZATION THEREOF

[75] Inventors: Akihiro Mizutani, Nagoya; Kimio Hirose, Gifu, both of Japan

[73] Assignee: Meito Sangyo Kabushiki Kaisha, Aichi, Japan

[21] Appl. No.: 274,067

[22] Filed: Jun. 16, 1981

[30] Foreign Application Priority Data

Jun. 16, 1980 [JP] Japan ................................. 55-80280
Oct. 20, 1980 [JP] Japan ................................ 55-145714

[51] Int. Cl.³ .................. A61K 31/70; A61K 31/715; C08B 37/02
[52] U.S. Cl. .................................... 424/180; 424/361; 424/70; 424/47; 536/112; 536/51; 536/114; 536/55.1
[58] Field of Search ................ 424/361, 180; 536/112, 536/51, 114, 43, 31, 55.1

[56] References Cited

U.S. PATENT DOCUMENTS

| 3,277,025 | 10/1966 | Flodin | 536/51 |
| 3,472,840 | 10/1969 | Stone et al. | 536/43 |
| 4,031,307 | 6/1977 | De Martino et al. | 536/114 |
| 4,160,826 | 7/1979 | Fischetti | 536/112 |
| 4,293,654 | 10/1981 | Levine et al. | 536/112 |

FOREIGN PATENT DOCUMENTS 50-53486   5/1975   Japan ..................... 536/112

Primary Examiner—Blondel Hazel
Attorney, Agent, or Firm—Sherman & Shalloway

[57] ABSTRACT

A cationized dextran of the following formula

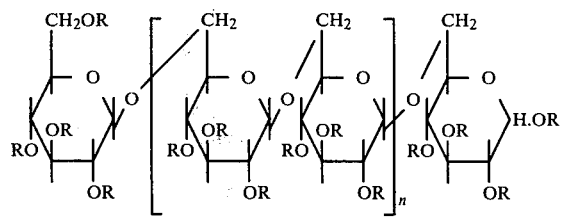

wherein R represents a group selected from the class consisting of a hydrogen atom, hydroxy lower alkyl groups, and quaternary nitrogen-containing groups of the formula

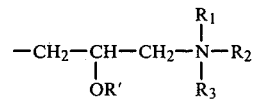

in which $R_1$, $R_2$ and $R_3$ each represent a lower alkyl group, and R' represents a hydrogen atom or a hydroxy lower alkyl group, and n is a positive number of from 1 to 8,000; two or more R groups may be identical or different provided that at least one of R groups is the quaternary nitrogen-containing group of the above formula;

and a salt thereof; a process for its production; and a hair or skin cosmetic composition containing aforesaid cationized dextran or its salt.

8 Claims, 9 Drawing Figures

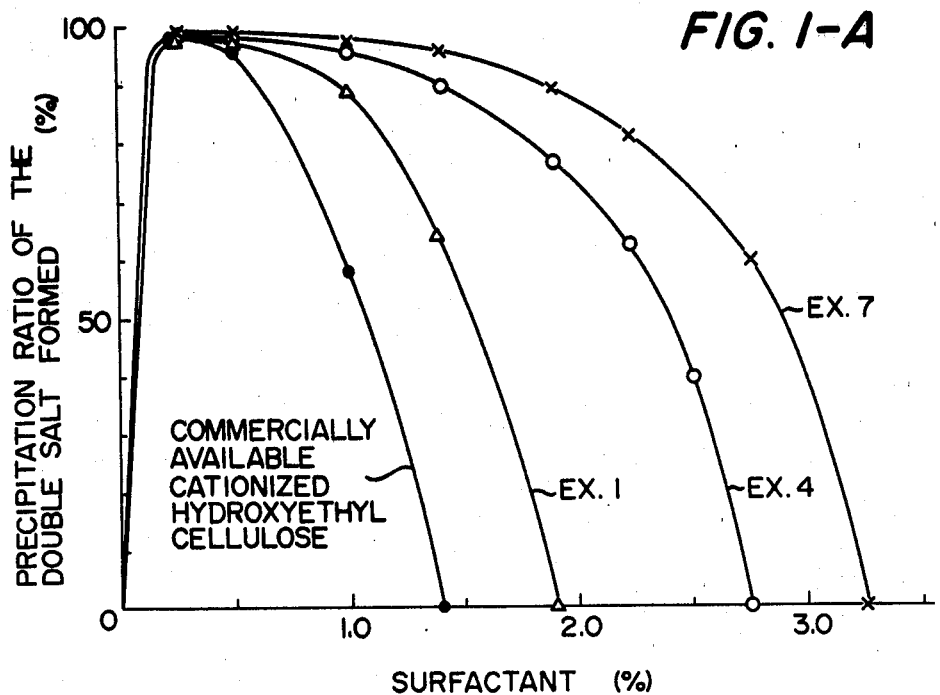
FIG. 1-A
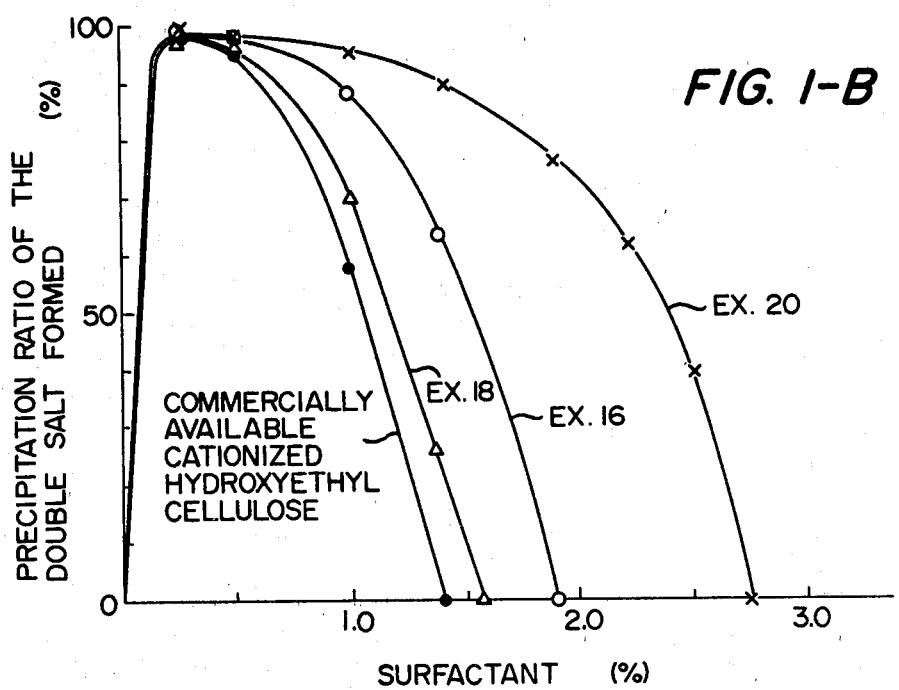
FIG. 1-B

CATIONIZED DEXTRAN AND SALTS THEREOF AND MANUFACTURING PROCESS AND UTILIZATION THEREOF

This invention relates to novel cationized dextran derivatives and their salts which can achieve various excellent improvements when incorporated in hair or skin cosmetic bases, and to a manufacturing process and utilization thereof. Specifically, it relates to cationized dextran derivatives and their salts which can be added to a wide range of bases, have a wide range of applicability and can achieve excellent improved results in regard to affinity with hair or skin, the suppleness, moisture-retaining property and feel of a film therefrom; and also to a process for their production and to their utilization.

Some proposals have been made heretofore about hair or skin cosmetics containing cation-modified polysaccharides.

Japanese Laid-Open Patent Publication No. 18641/1975 (corresponding to French Patent No. 2229390 and west German Patent No. 2423833) discloses a hair shampoo containing the quaternary nitrogen-containing cellulose ethers known from Japanese Patent Publication No. 20318/1970 (corresponding to U.S. Pat. No. 3,472,840). Japanese Laid-Open Patent Publication No. 11108/1979 discloses a hair shampoo containing a pullulan aminoalkyl ether. Japanese Laid-Open Patent Publication No. 129135/1979 discloses a hair shampoo containing hydroxyethyl cellulose or starch to which a quaternary nitrogen compound or a tertiary amine is added. Japanese Laid-Open Patent Publication No. 138133/1979 purposes a hair shampoo, hair rinse, hair treating agent, etc. containing a polypeptide and a quaternary nitrogen-containing cellulose ether. Japanese Laid-Open Patent Publication No. 157841/1979 discloses a hair conditioner containing an anionic surface-active agent and/or an amphoteric surface-active agent and a quaternary nitrogen-substituted cellulose ether and a hydrous alcohol. Japanese Laid-Open Patent Publication No. 36412/1980 discloses a hair shampoo, hair rinse and cleansing cream containing amylose or amylopectin substituted with a quaternary nitrogen-containing group. Furthermore, Japanese Laid-Open Patent Publication No. 45602/1980 discloses a hair or skin cosmetic such as shampoo, hair rinse, cleaning cream or neutral cream containing a cationized hydroxyalkyl starch substituted with a quaternary nitrogen-containing group.

It is said that the quaternary nitrogen-containing cationized polysaccharides used in the prior techniques cited above form double salts with surface-active agents, and the double salts formed are adsorbed, for example, onto the surface of the hair to provide a protective film.

However, the quaternary nitrogen-containing cationized polysaccharides in the above prior art have insufficient solubility in water, alcohols, etc., and the type of bases to which they can be added is very much limited. Hence, they can be used only within a limited range under limited conditions, and consequently are subject to many restrictions in their applicability. Moreover, their flocculating effect and antistatic effect and ability to form double salts with anionic or amphoteric surface-active agents, which may be attributed to cationization, are relatively low, and their adsorbability to hair, etc. is unsatisfactory. Moreover, they cannot have satisfactory feel during use, for example the smoothness of hair after use.

The present inventors made investigations in order to develop cationized polysaccharides which can overcome the aforesaid disadvantages or difficultites.

These investigations have led to the discovery that cationized dextrans of formula (1) and their salts can be easily produced; that these dextran derivatives and their salts which are not described in the literature can overcome the disadvantages and difficulties of the conventional compounds mentioned hereinabove; and that these compounds show many unique properties which cannot be attained by the conventional compounds.

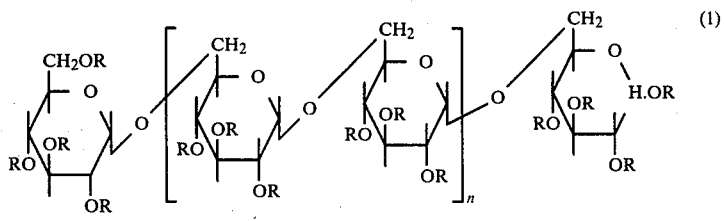

wherein R represents a group selected from the class consisting of a hydrogen atom, hydroxy lower alkyl groups, and quaternary nitrogen-containing groups of the formula

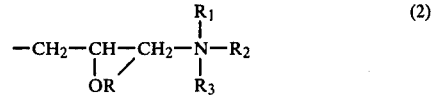

in which $R_1$, $R_2$ and $R_3$ each represent a lower alkyl group and R' represents a hydrogen atom or a hydroxy lower alkyl group, and n is a positive number of from 1 to 8,000; two or more R groups may be identical or different, provided that at least one of R groups is the group of formula (2) above.

Investigations of the present inventors have shown that the dextran derivatives of formula (1) and their salts have various unique properties. Particularly, they are readily soluble in water, and by suitably selecting their intrinsic viscosity, the degree of substitution of the quaternary nitrogen-containing group, the degree of substitution of the hydroxy lower alkyl group, etc., they are also readily soluble in solvents such as alcohols, and ketones. They also have excellent flocculating and antistatic effects, and can form double salts with anionic surfactants and amphoteric surfactants in a wider concentration range than the conventional cation-modified polysaccharides.

The conventional cation-modified polysaccharides, because of their low solubility, are ordinarily used in the form of double salts with anionic or amphoteric surfactants, and therefore their application to hair or skin cosmetic bases containing these surfactants is limited. In contrast, since the cationized dextran derivatives of formula (1) and their salts are well soluble by themselves in water, alcohols, ketones, etc., they can be broadly utilized in applications which do not use such surface active agents or should desirably not contain such surfactants, for example in hair conditioners, skin cosmetics, etc. Moreover, the cation-modified polysaccharides of the invention have excellent affinity with hair or skin, and can form films having suppleness and moisture-retaining property. Thus, the cationized dextran derivatives and their salts in accordance with this invention have been found to have a broad range of applicability.

In the cationized polysaccharides described in the prior literature, cellulose is a glucan having a $\beta$-1,4' linkage; amylose is a glucan having an $\alpha$-1,4' linkage; and amylopectin or pullulan is a glucan containing a major proportion of an $\alpha$-1,4' linkage and a minor proportion of an $\alpha$-1,6' linkage as a branched structure. In contrast, the cationized dextran of formula (1) is different in basic skeletal structure from the aforesaid conventional compounds in that the former is a compound resulting from the introduction of a quaternary nitrogen-containing group into dextran which is a glucan having an $\alpha$-1,6' linkage structure.

Accordingly, it is an object of this invention to provide the cationized dextran derivatives of formula (1) and their salts.

Another object of this invention is to provide a process for producing the cationized dextran derivatives of formula (1) and their salts.

Still another object of this invention is to provide a hair or skin cosmetic containing as an active ingredient at least one of the cationized dextran derivatives of formula (1) and their salts.

The above and other objects and advantages of this invention will become more apparent from the following description and the accompanying drawings in which:

FIG. 1-A is a graph plotting the precipitation ratio (%) of the double salt of the cationized dextran of the invention (Examples 1, 4 and 7) or of a commercially available cationized hydroxyethyl cellulose as a function of surfactant (%);

FIG. 1-B is a graph plotting the precipitation ratio (%) of the double salt of the cationized dextran of the invention (Examples 16, 18 and 20) or of a commercially available cationized hydroxyethyl cellulose as a function of surfactant (%);

Figure 2:
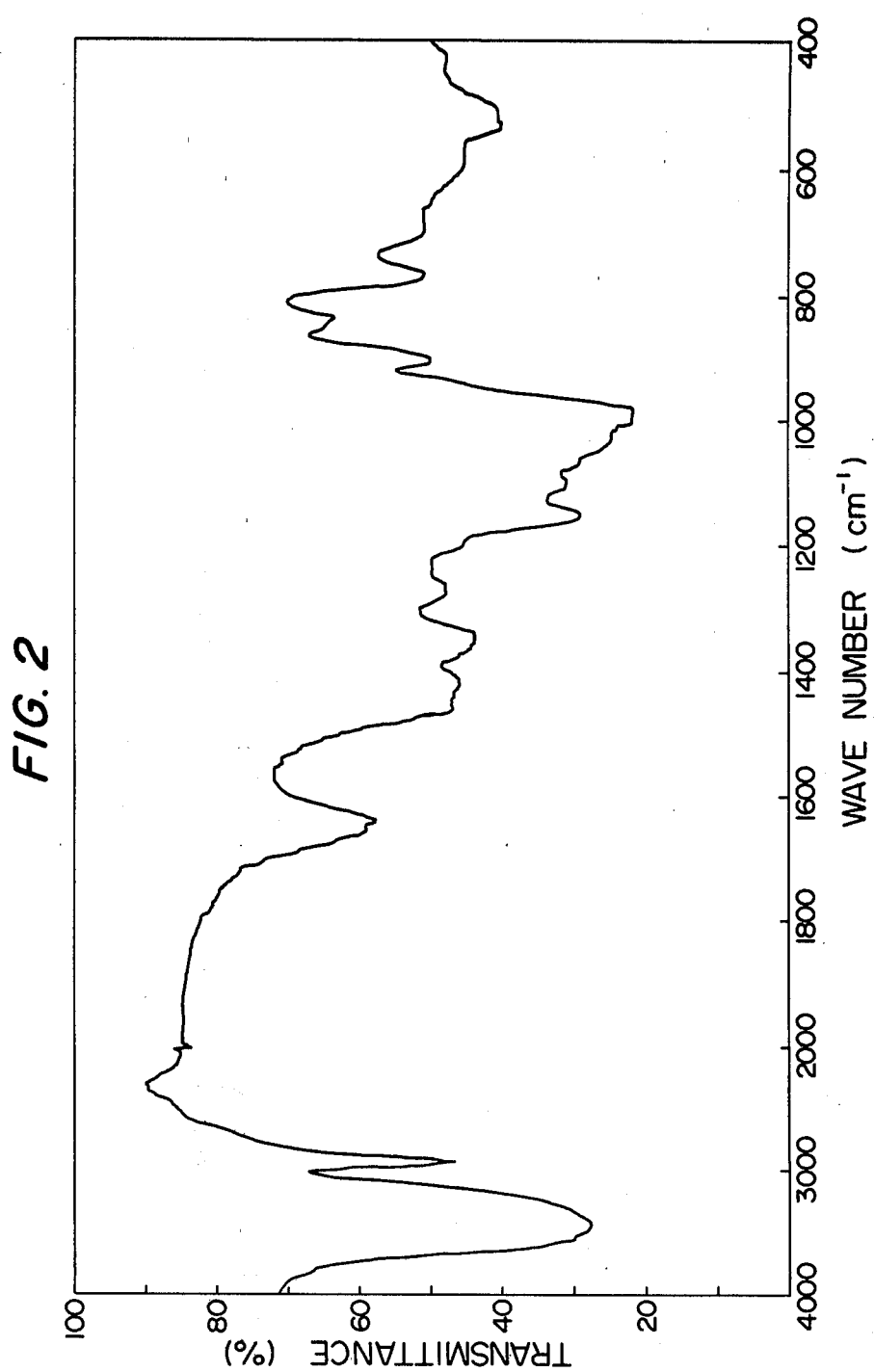
FIG. 2 is an infrared absorption spectral chart of the starting dextran used in Example 9.

The compound of formula (1) or its salt can be produced by reacting dextran with (i) a compound of the following formula (3)

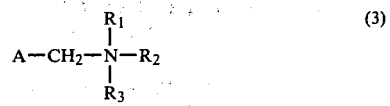

wherein each of $R_1$, $R_2$ and $R_3$ represents a lower alkyl group, and A represents

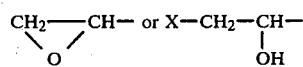

in which X is a halogen atom, or its salt; or (ii) the compound of formula (3) or its salt, and a hydroxy(lower)alkylating reagent in any sequence.

In the embodiment (ii), either the compound of formula (3) or its salt, or the alkylating reagent can be first reacted with dextran. Preferably, dextran is first reacted with the compound of formula (3) and then reacted with the alkylating reagent in view of the ease of reaction.

Typical examples of the compound of formula (3) are glycidyl tri-(lower alkyl) ammoniums and 3-halo-2-hydroxypropyl-tri-(lower alkyl) ammoniums.

In the formula representing the compound (3), the lower alkyl group is preferably an alkyl group having 1 to 4 carbon atoms, and examples of halogen are preferably chloro and bromo.

Examples of the compound of formula (3) or its salts include the following.
Glycidyl trimethyl ammonium,
glycidyl triethyl ammonium,
glycidyl tripropyl ammonium,
glycidyl ethyl dimethyl ammonium,
glycidyl diethyl methyl ammonium,
glycidyl tri-n-butyl ammonium,
glycidyl tri-iso-butyl ammonium,
3-chloro-2-hydroxypropyltrimethyl ammonium,
3-chloro-2-hydroxypropyltriethyl ammonium,
3-chloro-2-hydroxypropyltri-n-butyl ammonium,
3-chloro-2-hydroxypropyltri-iso-butyl ammonium,
3-bromo-2-hydroxypropyltrimethyl ammonium,
3-bromo-2-hydroxypropyltriethyl ammonium,
3-bromo-2-hydroxypropyltri-n-butyl ammonium,
3-bromo-2-hydroxypropyltri-iso-butyl ammonium,
and mineral salts and organic acid salts of the above compounds.

Examples of acids for forming the above inorganic or organic salts are hydrochloric acid, phosphoric acid, sulfuric acid, nitric acid, acetic acid and hydrobromic acid.

Alkyl groups having 1 to 4 carbon atoms, especially 1 to 3 carbon atoms, can be preferably cited as examples of the lower alkyl group in the hydroxy(lower)alkylating agent. Specific examples of such hydroxy(lower)alkylating agent are ethylene oxide, propylene oxide, ethylene chlorohydrin, ethylene bromohydrin and propylene chlorohydrin.

The reaction of dextran with the compound of formula (3) can be carried out, for example, by contacting dextran with the compound (3) in an aqueous medium. Specifically, the reaction can be carried out by dissolving or suspending dextran in an aqueous medium such as water or a mixture of water and an alcohol in the presence of an alkaline catalyst and then adding the compound of formula (3). Examples of the alkaline catalyst used in the reaction are hydroxides and carbonates of alkali metals such as sodium hydroxide, potassium hydroxide and sodium carbonate, and hydroxides of alkaline earth metals such as calcium hydroxide.

The reaction temperature is, for example, from about 0° C. to about 80° C. to 100° C., preferably from room temperature to about 60° to 70° C. The reaction time can be suitably selected, and is, for example, about 20 minutes to about 24 hours. After the reaction, the product is separated and purified as required by such means as filtration, dialysis and reprecipitation to give a cationized dextran derivative.

According to one example of the embodiment (ii), the cationized dextran obtained as above is first isolated and then reacted with the hydroxy(lower)alkylating agent. This is not particularly necessary, and the reaction mixture containing the cationized dextran may be directly subjected to the hydroxy(lower)alkylation reaction after adding an aqueous medium and/or an alkaline catalyst. The same can be said in the case of first performing the hydroxyalkylation reaction and then reacting the product with the compound of formula (3). The hydroxy alkylated product may be isolated and purified and then reacted with the compound of formula (3), or without performing such a purifying step, the hydroxy alkylation reaction mixture may be directly reacted with the compound of formula (3).

The reaction of dextran or the product obtained as above with the hydroxy(lower)alkylating reagent can be performed, for example, by contacting dextran or the above product with the hydroxyalkylating reagent in an aqueous medium. The reaction can be carried out in the presence of the alkaline catalyst exemplified hereinabove using the aqueous medium illustrated above. The reaction temperature is, for example, from about 0° C. to about 100° C., preferably from room temperature to about 70° C. The reaction time can be suitably selected, and is, for example, about 20 minutes to about 24 hours. Depending upon the reaction conditions, the hydroxyalkylating reagent might be polymerized in the above reaction. After the reaction, the reaction mixture may, as required, be purified by such means as filtration, dialysis and re-precipitation to isolate the desired product in pure form.

According to the process of this invention, cationized dextran derivatives of formula (1) having a substitution degree of up to 100% may be obtained. The substitution degree, as referred to herein, is defined as the ratio of the hydroxy(lower)alkyl groups and the quaternary nitrogen-containing groups of formula (2) to the total of the hydrogen atoms, hydroxy(lower)alkyl groups and the quaternary nitrogen-containing groups of formula (1) represented by R and R'. Suitable cationized dextran derivatives for use in skin and hair cosmetics have a substitution degree of about 3 to about 100%, preferably about 5 to about 95%. The dextran derivative of this invention can be obtained in any desired substitution degrees by properly adjusting the amounts of the compound of formula (3) and the hydroxy-alkylating agent.

The substitution degree can be calculated from the following equation after the nitrogen content (N%) of the cationized dextran derivative is measured by, for example, the Kjeldahl method and the content of hydroxy(lower)alkyl groups (H%) by, for example, the Morgan method.

$$\text{Substitution degree} = \frac{Q + Q'}{3 + Q} \times 100$$

Q and Q' are calculated from the following equations (A) and (B).

$$\frac{\text{Atomic weight of N atoms} \times Q}{162 + (\text{the molecular weight of the quaternary nitrogen-containing group} - 1) \times Q + (\text{the molecular weight of the hydroxy(lower)alkyl group} - 1) \times Q'} \times 100 = N\% \quad (A)$$

$$\frac{\text{Molecular weight of the hydroxy(lower)alkyl group} \times Q'}{162 + (\text{the molecular weight of the quaternary nitrogen-containing group} - 1) \times Q + (\text{the molecular weight of the hydroxyl (lower)alkyl group} - 1) \times Q'} \times 100 = H\% \quad (B)$$

Since the cationized dextran derivative is a polymeric electrolyte and its degree of polymerization is polydisperse, n in formula (1) represents the average degree of polymerization. The parameter which represents the average degree n of polymerization of the cationized dextran derivative is intrinsic viscosity ($\eta$). Accordingly, the average degree of polymerization can be known from the relation of the average molecular weight of the starting dextran to the intrinsic viscosity of the cationized dextran.

The average molecular weight of the starting dextran can be determined by measuring its intrinsic viscosity in the following manner and applying it to the Sato's equation (Polymer Chemistry, Vol. 13, No. 14, Page 526) given below.

Specifically, dextran is dissolved in water to form a sample solution. The flowing times of the sample solution and water are measured at 25°±0.02° C. by means of an Ubbelohde's viscometer and then the viscosity [$\eta$] of the dextran is calculated from the following equation.

$$\text{Intrinsic viscosity } (\eta) = \frac{l_n \frac{\text{Flowing time of the sample solution (sec.)}}{\text{Flowing time of water (sec.)}}}{\text{Amount of the sample solution (g/dl)}}$$

Using the intrinsic viscosity value thus calculated, the average molecular weight M of the starting dextran is calculated from the following Sato's equation.

$$[\eta] = 9.00 \times 10^{-4} M^{0.50}$$

In the present invention, the intrinsic viscosity of the cationized dextran derivative of formula (1) can be measured in the same way as above using a solution of the sample in a 1 M sodium chloride solution, and a 1 M sodium chloride solution.

For simplicity, the intrinsic viscosity ($\eta$) may be substituted for the n value in the cationized dextran derivative of formula (1). For example, a cationized dextran derivative of formula (1) having a quaternary nitrogen-containing group substitution degree of about 5 to 33%, a hydroxyloweralkyl group substitution degree of about 0 to about 90% with the total substitution degree being about 5 to about 95% and an n value of about 3 to about 5,500 has an intrinsic viscosity ($\eta$) of about 0.04 to about 2.0. The n value of 1 to 8,000 in formula (1) corresponds to an intrinsic viscosity ($\eta$) of about 0.02 to about 2.3.

Such a cationized dextran derivative can be produced by selecting dextran having an average molecular weight of about 640 to about 2.5 million. Accordingly, instead of n=1 to 8,000 in formula (1), n may be defined as a positive number which provides a cationized dextran derivative of formula (1) having an intrinsic viscosity ($\eta$) of about 0.02 to about 2.3.

The cationized dextran derivative of formula (1) may be in the form of its salt. For use in hair or skin cosmetics, it is used in the form of a salt acceptable for hair or skin cosmetics.

Examples of such a salt and a process for production thereof are described below.

When the salts exemplified hereinabove are used as the compound of formula (3), the same salts as these can be obtained. Furthermore, the product may be converted to a desired salt by ion-exchanging. For example, when glycidyl methyl ammonium chloride is used as the compound of formula (3), the resulting cationized dextran derivative is a hydrochloride. For example, a solution of the product is treated with a conventional anion exchange resin, and a large amount of the desired anion is added. Then, the mixture is subjected to such a means as dialysis and re-precipitation to convert it to another desired salt. The anion may, for example, be an inorganic or organic acid anion, such as a phosphite, sulfite, nitrate, acetate, citrate, oxalate or malonate.

The cationized dextran derivatives of formula (1) and their salts are more soluble in water, alcohols and ketones than cationized celluloses and cationized starches which have previously been utilized and proposed, and can be used in shampoos, rinses and hair treating agents. They are also suitable for incorporation in hair or skin cosmetics such as hair conditioners, hair tonics, cleansing creams and neutral creams to which the conventional cationized polysaccharides are difficult to add. Furthermore, as shown in FIGS. 1-A and 1-B of the accompanying drawings, the compounds of this invention can form stable double salts with surfactants in a broader range of concentrations than can the conventional other cationized polysaccharides.

While the double salts of the conventional cationized polysaccharides with surfactants are solid, the double salts of the cationized dextran derivatives of the invention are viscous syrups and can form uniform, thin and supple films.

Thus, according to this invention, there can be provided a hair or skin cosmetic composition comprising a hair or skin cosmetic base and at least one of the cationized dextran derivatives of formula (1), preferably those having a quaternary nitrogen substitution degree of about 3 to about 33 to about 40%, a hydroxy lower alkyl group substitution degree of 0 to about 90%, for example about 5 to about 90%, with the total substitution degree being about 5 to about 95% and an n value of 4 to 6,000 corresponding to an intrinsic viscosity ($\eta$) of from about 0.04 to about 1.85 to about 2.1, or the salts thereof acceptable for hair or skin cosmetics.

The amount of the cationized dextran derivative of formula (1) to be added to the cosmetic base can be suitably selected, but is, for example, from about 0.1 to about 5% by weight.

The cationized dextran derivatives of this invention have superior solubility in water, alcohols and ketones, superior flocculating property, superior antistatic effect, an excellent ability to form double salts with anionic or amphoteric surfactants, and an excellent ability to form protective colloids and films. Hence, they are also useful in toiletry agents (such as detergents), pharmaceutical bases, floculants, thickeners, papermaking aids, and paint additives.

The following Examples illustrate the present invention more specifically.

EXAMPLE 1

A 1-liter reactor equipped with a stirrer and a condenser was charged with 81 g of dextran having an average molecular weight of about 1,810 and 100 ml of water.

Then, 110 ml of a 40% by weight aqueous solution of sodium hydroxide was added, and the mixture was stirred for 10 minutes. Then, 250 ml of an aqueous solution containing 188 g of 3-chloro-2-hydroxypropyltrimethyl ammonium chloride was added. The mixture was heated to 50° C., and reacted for 3 hours. The reaction mixture was neutralized with hydrochloric acid.

The reaction mixture was precipitated three times with ether from water and methanol, and dried in vacuum at 50° C. to give 58 g of a white powder of pure cationized dextran hydrochloride being soluble in water and ethanol and having a quaternary nitrogen substitution degree of 19.0%, an intrinsic viscosity ($\eta$) of 0.05 (n=4.5) and a specific rotation $(\alpha)_D^{20}$ of $+114°$.

EXAMPLE 2

Example 1 was repeated except that 81 g of dextran having an average molecular weight of about 10,450 was used as the starting material. There was obtained 84 g of a white powder of pure cationized dextran hydrochloride being soluble in water and ethanol and having a quaternary nitrogen substitution degree of 17.1%, an intrinsic viscosity ($\eta$) of 0.11 (n=31.2) and a specific rotation $(\alpha)_D^{20}$ of $+120°$.

EXAMPLE 3

Example 1 was repeated except that 81 g of dextran having an average molecular weight of about 59,000 and 150 ml of water were used. There was obtained 100 g of a white powder of pure cationized dextran hydrochloride being soluble in water and ethanol and having a quaternary nitrogen substitution degree of 16.0%, an intrinsic viscosity ($\eta$) of 0.34 (n=181) and a specific rotation $(\alpha)_D^{20}$ of $+126°$.

EXAMPLE 4

Example 1 was repeated except that 81 g of dextran having an average molecular weight of about 664,000 and 300 ml of water were used. There was obtained 102 g of a white powder of purified cationized dextran hydrochloride having a quaternary nitrogen substitution degree of 14.0%, an intrinsic viscosity of 0.45 (n=2048) and a specific rotation $(\alpha)_D^{20}$ of $+122°$.

EXAMPLE 5

Example 1 was repeated except that 81 g of dextran having an average molecular weight of about 1,660,000 and 500 ml of water were used. There was obtained 96 g of a white powder of pure cationized dextran hydrochloride having a quaternary nitrogen substitution degree of 11.5%, an intrinsic viscosity ($\eta$) of 1.51 (n=5122) and a specific rotation $(\alpha)_D^{20}$ of $+136°$

EXAMPLE 6

81 g of dextran having an average molecular weight of about 59,000 and 300 ml of water were charged.

Then, 5 ml of a 40% by weight aqueous solution of sodium hydroxide was added and the mixture was stirred for 10 minutes. 180 ml of an aqueous solution containing 76 g of glycidyl trimethyl ammonium chloride was added. The mixture was heated to 60° C. and reacted for 5 hours. The reaction mixture was neutralized with acetic acid, and dialyzed against flowing water for 24 hours. The dialyzate was lyophilized to give 92 g of a white powder of pure cationized dextran hydrochloride having a quaternary nitrogen substitution degree of 6.9%, an intrinsic viscosity ($\eta$) of 0.18 (n=181) and a specific rotation $(\alpha)_D^{20}$ of +163°.

EXAMPLE 7

81 g of dextran having an average molecular weight of about 59,000 and 200 ml of water were charged. Then, 25 ml of a 40% by weight aqueous solution of sodium hydroxide was added. The mixture was stirred for 10 minutes, and 900 ml of an aqueous solution containing 379 g of glycidyl trimethyl ammonium chloride was added. The mixture was worked up in the same way as in Example 6 to give 138 g of a white powder of pure cationized dextran hydrochloride soluble in water and ethanol and having a quaternary nitrogen substitution degree of 28.3%, an intrinsic viscosity of 0.51 (n=181) and a specific rotation $(\alpha)_D^{20}$ of +95°.

EXAMPLE 8

81 g of dextran having an average molecular weight of about 664,000 and 1,000 ml of water were charged. Then, 30 ml of a 40% by weight aqueous solution of sodium hydroxide was added, and the mixture was stirred for 10 minutes. Then, 1,080 ml of an aqueous solution containing 455 g of glycidyl trimethyl ammonium chloride was added. The mixture was then worked up in the same way as in Example 6 to give 130 g of a white powder of pure cationized dextran hydrochloride being soluble in water and ethanol and having a quaternary nitrogen substitution degree of 24.2%, an intrinsic viscosity of 0.69 (n=2048) and a specific rotation of +93°.

EXAMPLE 9

81 g of dextran having an average molecular weight of about 1,660,000 and 1,000 ml of water were charged. Then, 330 ml of a 40% by weight aqueous solution of sodium hydroxide was added. The mixture was stirred for 10 minutes. Then, 750 ml of an aqueous solution containing 564 g of 3-chloro-2-hydroxypropyltrimethyl ammonium chloride was added. The mixture was worked up in the same way as in Example 1 to give 113 g of a white powder of pure cationized dextran hydrochloride having a quaternary nitrogen substitution degree of 22.9%, an intrinsic viscosity of 1.88 (n=5122) and a specific rotation of +95°.

EXAMPLE 10

81 g of dextran having an average molecular weight of about 59,000 and 100 ml of water were charged. Then, 350 ml of a 50% by weight aqueous solution of sodium hydroxide was added, and the mixture was stirred for 10 minutes. Further, 1,000 ml of an aqueous solution containing 752 g of 3-chloro-2-hydroxypropyl-trimethyl ammonium chloride was added. The mixture was heated to 50° C. and reacted for 8 hours. The reaction mixture was worked up in the same way as in Example 6 to give 159 g of a white powder of pure cationized dextran hydrochloride soluble in water and ethanol and having a quaternary nitrogen substitution degree of 39.2%, an intrinsic viscosity of 0.88 (n=181) and a specific rotation of +77°.

EXAMPLE 11

81 g of dextran having an average molecular weight of about 10,450 and 100 ml of water were charged. Then, 110 ml of a 40% by weight aqueous solution of sodium hydroxide was added, and the mixture was stirred for 10 minutes. 250 ml of an aqueous solution containing 230 g of 3-chloro-2-hydroxy-propyltriethyl ammonium chloride was added. The mixture was then worked up in the same way as in Example 6 to give 110 g of a white powder of pure cationized dextran hydrochloride being soluble in water and ethanol and having a quaternary nitrogen substitution degree of 14.9%, an intrinsic viscosity of 0.14 (n=31.2) and a specific rotation of +105°.

EXAMPLE 12

81 g of dextran having an average molecular weight of about 59,000 and 100 ml of water were charged. Then, 200 ml of a 40% by weight aqueous solution of sodium hydroxide was added, and the mixture was stirred for 10 minutes. Then, 700 ml of an aqueous solution containing 387 g of glycidyl triethyl ammonium chloride was added. The mixture was heated to 60° C. and reacted for 4 hours. The reaction mixture was worked up in the same way as in Example 6 to give 135 g of a white powder of pure cationized dextran hydrochloride being soluble in water and ethanol and having a quaternary nitrogen substitution degree of 22.0%, an intrinsic viscosity of 0.43 (n=181) and a specific rotation of +84°.

EXAMPLE 13

The cationized dextran hydrochloride obtained in Example 2 was dissolved in water, and the solution was passed through a column of a cation exchange resin (Amberlite IR-120B, a registered trademark for a product of Tokyo Organic Chemistry Industry Co., Ltd.). The effluent was neutralized with citric acid and lyophilized to give 85 g of a white powder of cationized dextran citrate being soluble in water and ethanol and having a quaternary nitrogen substitution degree of 17.1%, an intrinsic viscosity of 0.12 (n=31.2) and a specific rotation of +118°.

FORMULATION EXAMPLE 1

Shampoos having the compositions (A) to (G) shown in Table 1 were prepared using the cationized dextran derivatives obtained in the above Examples. As a comparison, a shampoo not containing a cationized dextran derivative was prepared. The various properties of the shampoos, such as smoothness during use, hair creaking during rinsing, and the softness and gloss of hair on finishing, were tested, and the results are shown in Table 1.

The standards of evaluation of these properties were as follows:

| | Smoothness during use |
|---|---|
| O | Good |
| Δ | Fairly good |
| X | Poor |
| | Hair Creaking during rinsing |
| O | Did not occur. |
| Δ | Slightly occurred. |

-continued

| | |
|---|---|
| X | Occurred. |

Softness, ease of grooming, ease of combing, and gloss of hair on finishing

○ Good
△ Fairly good
X Poor

The results given in Table 1 show that the shampoos containing the cationized dextran derivatives have superior hand to that not containing a cationized dextran derivative during use, rinsing and finishing.

FORMULATION EXAMPLE 3

Hair treating agents have the compositions (A) to (D) shown in Table 3 were prepared by using the cationized dextran derivatives obtained in the above Examples. As a comparison, a hair treating agent not containing a cationized dextran derivative was prepared. The properties of the hair treating agents (the softness, ease of grooming, gloss and ease of combing of hair after use) were tested, and the results are shown in Table 3.

The standards of evaluation were the same as in Formulation Example 1.

TABLE 1

| | Recipe Amount (% by weight) | | | | | | | |
|---|---|---|---|---|---|---|---|---|
| Component | (A) | (B) | (C) | (D) | (E) | (F) | (G) | Comparison |
| Polyoxyethylene lauryl ether sulfate sodium salt ($\overline{P}=3$) | 7.5 | 7.5 | 7.5 | 7.5 | 7.5 | 7.5 | 7.5 | 7.5 |
| 2-lauryl-N—carboxymethyl-N—hydroxy-ethyl imidazolium betaine | 10 | 10 | 10 | 10 | 10 | 10 | 10 | 10 |
| Coconut oil fatty acid diethanolamide | 3 | 3 | 3 | 3 | 3 | 3 | 3 | 3 |
| Cationized dextran (Example No.) | 1 | 3 | 4 | 5 | 7 | 11 | 12 | — |
| Amount of the cationized dextran | 1 | 1 | 0.5 | 0.3 | 0.2 | 0.5 | 0.5 | 0 |
| Perfume, coloring agent, antiseptic | suitable amount | suitable amount | suitable amount | suitable amount | suitable amount | suitable amount | suitable amount | suitable amount |
| Purified water | balance | balance | balance | balance | balance | balance | balance | balance |
| Smoothness during use | ○ | ○ | ○ | ○ | ○ | ○ | ○ | △ |
| Hair creaking during rinsing | ○ | ○ | ○ | ○ | ○ | ○ | ○ | X |
| Softness of hair on finishing | ○ | ○ | ○ | ○ | ○ | ○ | ○ | X |
| Ease of grooming on finishing | ○ | ○ | ○ | ○ | ○ | ○ | ○ | X |
| Gloss of hair on finishing | ○ | ○ | ○ | ○ | ○ | ○ | ○ | △ |
| Ease of combing on finishing | ○ | ○ | ○ | ○ | ○ | ○ | ○ | X |

FORMULATION EXAMPLE 2

Hair rinses having the compositions (A) to (F) shown in Table 2 were prepared using the cationized dextran derivatives obtained in the above Examples. As a comparison, a hair rinse not containing a cationized dextran derivative was prepared. The properties of the hair rinses, such as the softness and gloss of hair on finishing, were tested, and the results are shown in Table 2.

TABLE 2

| | Recipe Amount (% by weight) | | | | | | |
|---|---|---|---|---|---|---|---|
| Component | (A) | (B) | (C) | (D) | (E) | (F) | Comparison |
| Distearyl dimethyl ammonium chloride | 5 | 5 | 5 | 5 | 5 | 5 | 5 |
| Cetyl alcohol | 3 | 3 | 3 | 3 | 3 | 3 | 3 |
| Propylene glycol | 6 | 6 | 6 | 6 | 6 | 6 | 6 |
| Polyoxyethylene oleyl alcohol | 1 | 1 | 1 | 1 | 1 | 1 | 1 |
| 2-Hexyldecanol | 1 | 1 | 1 | 1 | 1 | 1 | 1 |
| Cationized dextran (Example No.) | 2 | 6 | 8 | 9 | 10 | 12 | — |
| Amount of the cationized dextran | 3 | 3 | 1 | 1 | 1 | 1 | 0 |
| Perfume, coloring agent, antiseptic | suitable amount | suitable amount | suitable amount | suitable amount | suitable amount | suitable amount | suitable amount |
| Purified water | balance | balance | balance | balance | balance | balance | balance |
| Softness of hair on finishing | ○ | ○ | ○ | ○ | ○ | ○ | △ |
| Ease of grooming on finishing | ○ | ○ | ○ | ○ | ○ | ○ | △ |
| Gloss of hair on finishing | ○ | ○ | ○ | ○ | ○ | ○ | △ |
| Ease of combing on finishing | ○ | ○ | ○ | ○ | ○ | ○ | X |

The standards of evaluation were the same as in Formulation Example 1.

The results given in Table 2 show that the hair rinses containing the cationized dextran derivatives give better feel to hair than that not containing a cationized dextran derivative at the time of finishing.

TABLE 3

| | Recipe Amount (% by weight) | | | | |
|---|---|---|---|---|---|
| Component | (A) | (B) | (C) | (D) | Comparison |
| Liquid lanolin | 1.5 | 1.5 | 1.5 | 1.5 | 1.5 |
| Cetanol | 7.5 | 7.5 | 7.5 | 7.5 | 7.5 |
| 2-Hexyldecanol | 9 | 9 | 9 | 9 | 9 |
| Polyoxyethylene- oleyl ether | 6 | 6 | 6 | 6 | 6 |
| Stearyldimethyl ammonium chloride | 6 | 6 | 6 | 6 | 6 |
| Glycerol | 3 | 3 | 3 | 3 | 3 |
| Cationized dextran (Example No.) | 1 | 7 | 10 | 12 | — |
| Amount of the | 2 | 1 | 0.5 | 0.5 | 0 |

TABLE 3-continued

| | Recipe | | | | |
| | Amount (% by weight) | | | | |
| Component | (A) | (B) | (C) | (D) | Comparison |
|---|---|---|---|---|---|
| cationized dextran | | | | | |
| Perfume, coloring agent, antiseptic | suitable amount | suitable amount | suitable amount | suitable amount | suitable amount |
| Purified water | balance | balance | balance | balance | balance |
| Softness of hair on finishing | O | O | O | O | Δ |
| Ease of grooming on finishing | O | O | O | O | Δ |
| Gloss of hair on finishing | O | O | O | O | Δ |
| Ease of combing on finishing | O | O | O | O | Δ |

The results given in Table 3 demonstrate that the hair treating agents containing the cationized dextran derivatives give better feel to hair after use than that not containing a cationized dextran derivative.

FORMULATION EXAMPLE 4

Hair tonics having the compositions (A) and (B) in Table 4 were prepared by using the cationized dextran derivatives obtained in the above Examples. As a comparison, a hair tonic not containing a cationized dextran derivative was prepared. The properties of the hair tonics (the ease of grooming, gloss and ease of combing of hair after use), were tested, and the results are shown in Table 4. The standards of evaluation were the same as in Formulation Example 1.

TABLE 4

| | Recipe | | |
| | Amounts blended (wt. %) | | |
| Components | (A) | (B) | Comparison |
|---|---|---|---|
| Modified ethanol | 60 | 60 | 60 |
| Menthol | 0.2 | 0.2 | 0.2 |
| Castor oil | 2 | 2 | 2 |
| Polyoxyethylene lauryl ether sodium phosphate | 2 | 2 | 2 |
| Salicylic acid | 0.1 | 0.1 | 0.1 |
| Cationized dextran (Example No.) | 8 | 11 | none |
| Amount of the cationized dextran | 1 | 1 | 0 |
| Perfume | suitable amount | suitable amount | suitable amount |
| Purified water | balance | balance | balance |
| Ease of hair grooming after use | O | O | X |
| Gloss of hair after use | O | O | X |
| Ease of combing after use | O | O | Δ |

FORMULATION EXAMPLE 5

An aerosol lacquer having the following formulation was prepared using the cationized dextran derivative obtained in Example 12.

| Component | Amount (% by weight) |
|---|---|
| Cationized dextran | 4 |
| Perfume | 0.2 |
| Ethanol | balance |

Trichloromonofluoromethane (47 g) and 28 g of dichlorodifluoromethane were added to 25 g of the above solution to prepare an aerosol lacquer in a container.

When it was sprayed onto the hair, a soft touch was obtained with good combability and gloss.

FORMULATION EXAMPLE 6

Using the cationized dextran derivative obtained in Example 8, a hairdressing lotion having the following formulation was prepared.

| Component | Amount (% by weight) |
|---|---|
| Ethanol | 50 |
| Perfume and dye | suitable amounts |
| Cationized dextran | 3 |
| Purified water | balance |

When the resulting lotion was applied to the hair in a usual manner, good combability was obtained with good gloss. These properties lasted for an extended period of time.

FORMULATION EXAMPLE 7

In accordance with the following formulation, the cationized dextran derivative obtained in Example 3 was combined with an imidazoline-type amphoteric surfactant to form a double salt. The double salt was uniformly dissolved in a mixture of ethanol and water to prepare a dispenser-type hair conditioner.

| Component | Amount (% by weight) |
|---|---|
| Cationized dextran | 0.5 |
| Imidazoline-type amphoteric surfactant (2-alkyl-N—carboxymethyl-N—hydroxyethyl-imidazolium betaine) | 0.5 |
| Ethanol/water (80/20) | 99 |

When this hair conditioner was applied to the hair in a usual manner, good combability was obtained with gloss and wet feeling.

FORMULATION EXAMPLE 8

A cleansing cream having the following formulation was prepared by using the cationized dextran derivative obtained in Example 11.

| Component | Amount (% by weight) |
|---|---|
| Liquid paraffin | 40 |
| Solid paraffin | 10 |
| Vaseline | 15 |
| Beeswax | 3 |
| Sorbitan sesquioleate | 4 |
| Polyoxyethylene sorbitan monoleate | 1 |
| Perfume, antioxidant and antiseptic | suitable amounts |
| Cationized dextran | 1.5 |
| Purified water | balance |

This cream had better spreadability and oily feeling than a cream not containing the cationized dextran.

FORMULATION EXAMPLE 9

A neutral cream having the formulations shown below was prepared by using the cationized dextran derivative obtained in Example 1.

| Component | Amount (% by weight) |
|---|---|
| Liquid paraffin | 10 |
| Vaseline | 10 |
| Glycerol monostearate | 0.5 |
| Isopropyl palmitate | 2 |
| Glycerol | 3 |
| Perfume, antioxidant, antiseptic | suitable amounts |
| Cationized dextran | 1 |
| Purified water | balance |

This cream had better smoothness and wet feeling than a cream not containing the cationized dextran.

FIG. 1-A shows the mutual action of a cationized polysaccharide and an imidazoline-type amphoteric surfactant (SOFTAZOLINE CL, a tradename for a product of Kawaken Fine Chemical, Co., Ltd.), which was measured under the following measuring conditions.

Measuring conditions: A 5% solution of SOFTAZOLINE CL was added to a 0.1% solution of the cationized polysaccharide, and the amount of the precipitated double salt was measured.

FIG. 2 is an infrared absorption spectral chart of the starting dextran used in Example 9.

| 3800–3200 cm$^{-1}$: | —OH |
|---|---|
| 1200–1050 cm$^{-1}$: | —CO |
| 910, 840, 770 cm$^{-1}$: | α-1,6' linkage |

Figure 3:
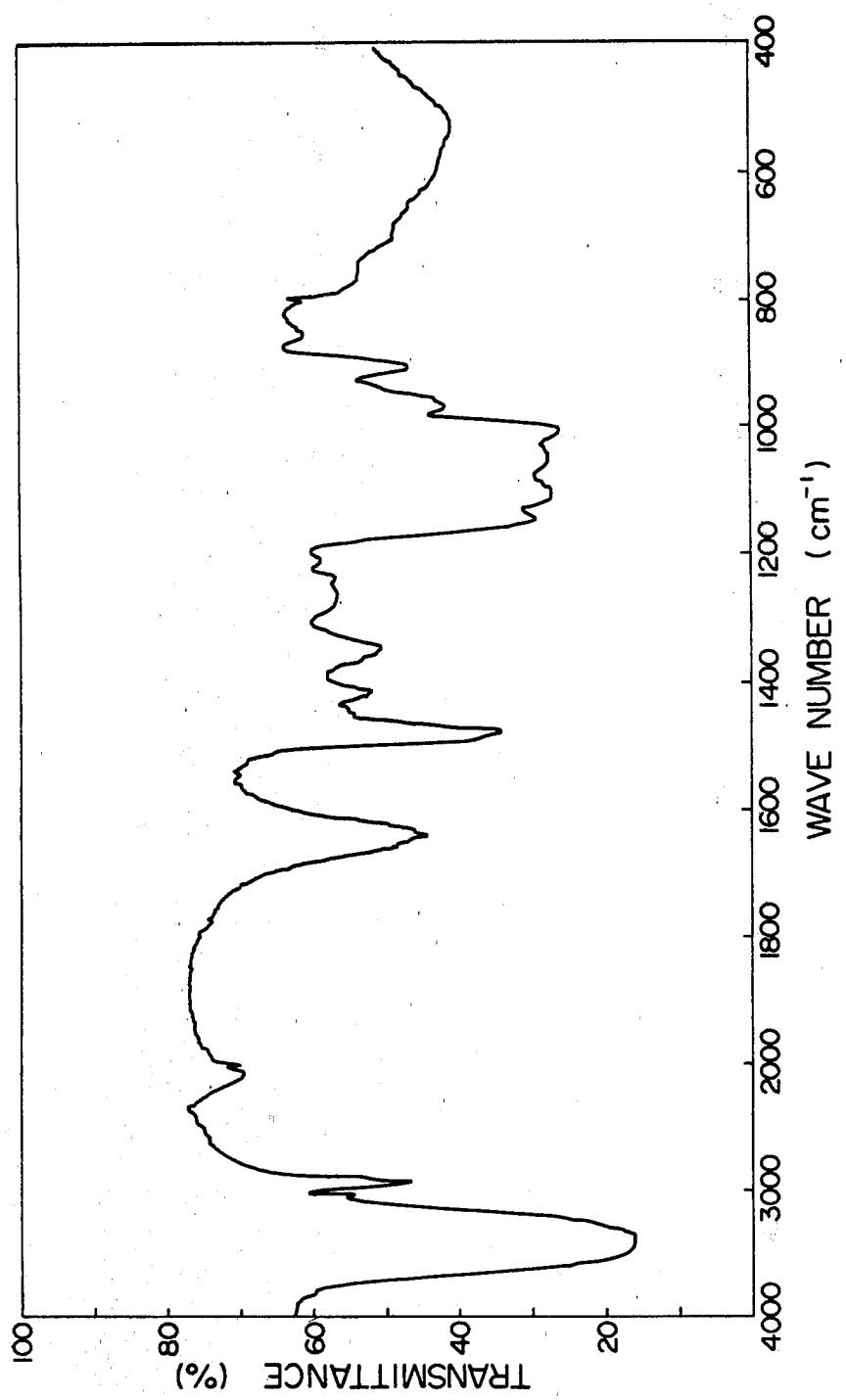
FIG. 3 is an infrared absorption spectral chart of the cationized dextran obtained in Example 9.

FIG. 3 is an infrared absorption spectrum of the cationized dextran hydrochloride obtained in Example 9.

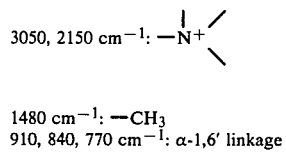

Figure 4:
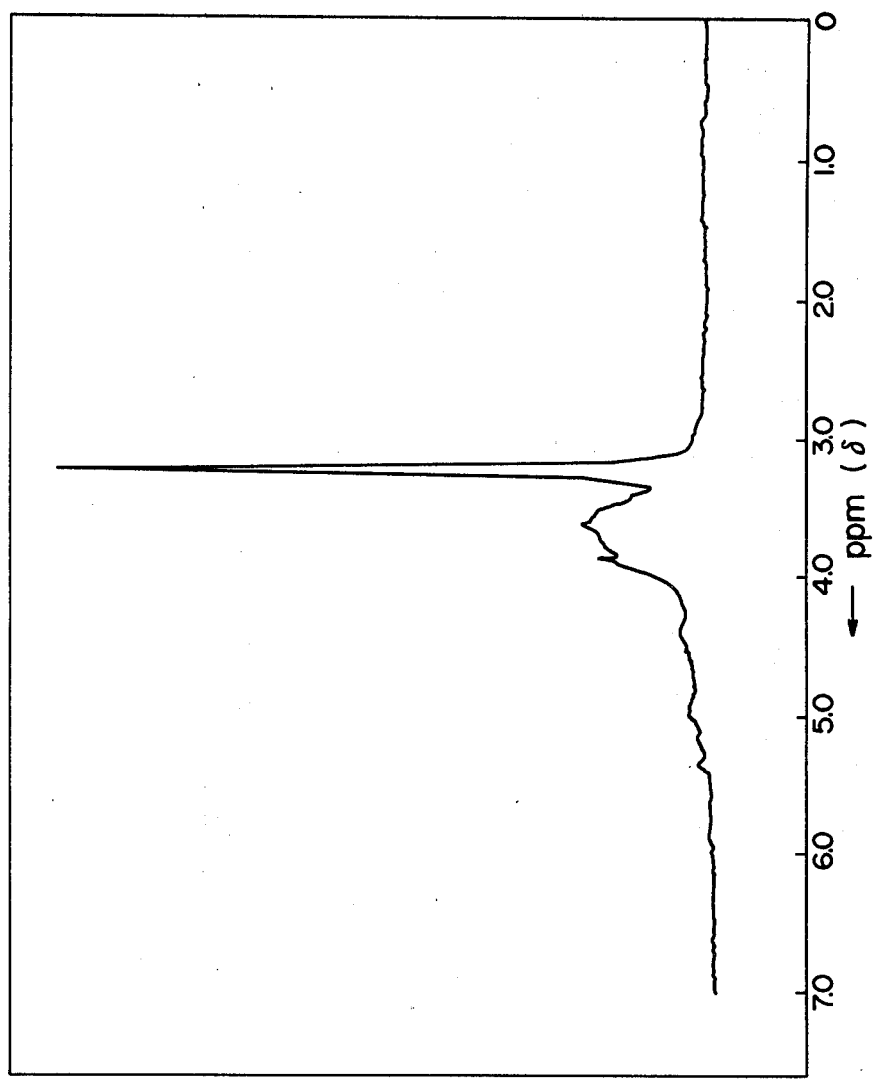
FIG. 4 is a nuclear magnetic resonance spectral chart of the cationized dextran hydrochloride obtained in Example 4.

3050, 2150 cm$^{-1}$: —N$^+$ 1480 cm$^{-1}$: —CH$_3$
910, 840, 770 cm$^{-1}$: α-1,6' linkage FIG. 4 is a nuclear magnetic resonance spectral chart of the cationized dextran hydrochloride obtained in Example 4.

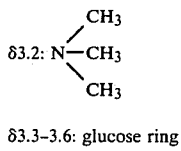

δ3.3–3.6: glucose ring

Figure 5:
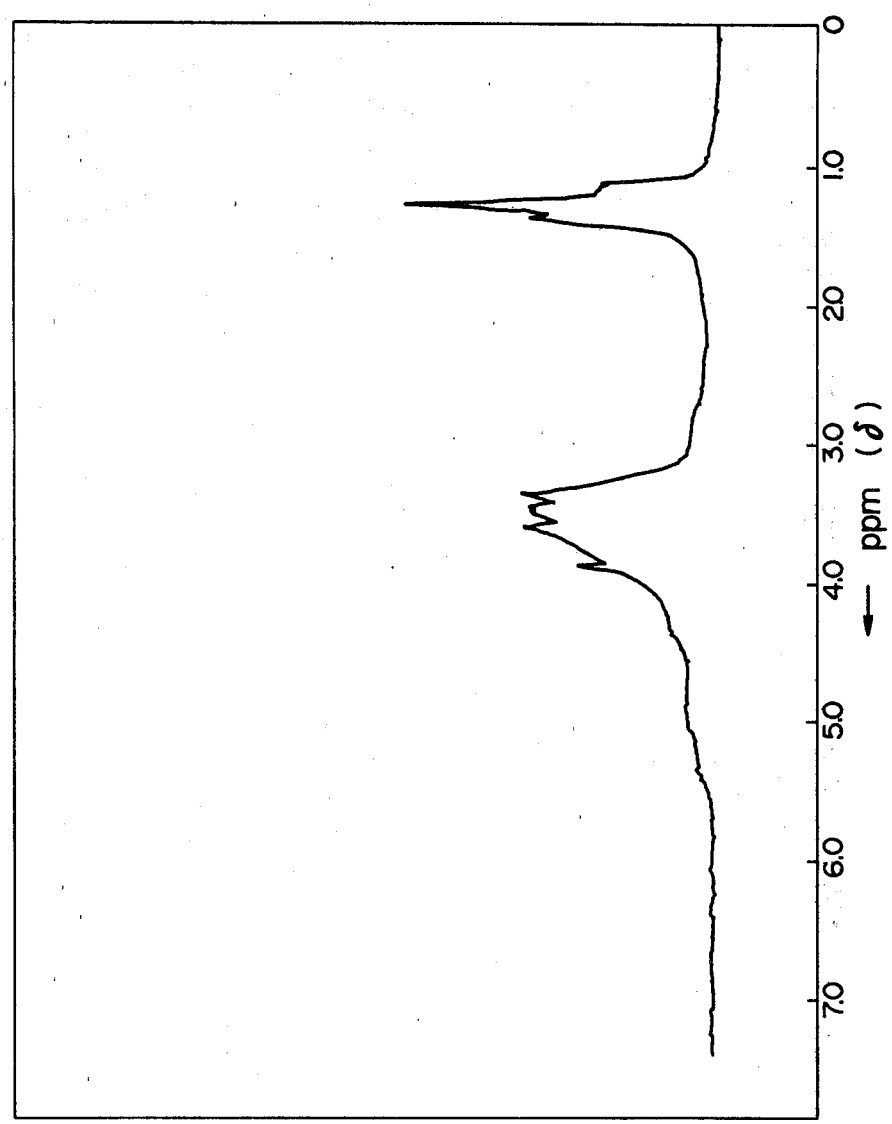
FIG. 5 is a nuclear magnetic resonance spectral chart of the cationized dextran obtained in Example 12.

FIG. 5 is a nuclear magnetic resonance spectral chart of the cationized dextran obtained in Example 12.

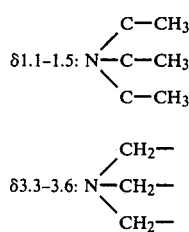

δ3.3–5.2: glucose ring

EXAMPLE 14

A 2-liter closed reactor equipped with a stirrer was charged with 81 g of dextran having an average molecular weight of about 1,810 and 100 ml of water. Then, 110 ml of a 40% aqueous solution of sodium hydroxide was added, and the mixture was stirred for 10 minutes. Further, 250 ml of an aqueous solution containing 188 g of 3-chloro-2-hydroxypropyltrimethyl ammonium chloride was added. The mixture was heated to 50° C., and reacted for 3 hours. 174 g of propyleneoxide was added, and the mixture was heated to 50° C. and reacted for 3 hours. The reaction mixture was neutralized with hydrochloric acid, and dialyzed against flowing water for 24 hours. The dialyzate was lyophilized to give 105 g of a white powder of pure cationized dextran being soluble in water, ethanol and acetone and having a quaternary nitrogen substitution degree of 18.3%, a hydroxypropyl substitution degree of 74%, an intrinsic viscosity of 0.07 (n=4.5) and a specific rotation of +80°.

EXAMPLE 15

Example 14 was repeated except that 81 g of dextran having an average molecular weight of about 10,450 was used. There was obtained a white powder of pure cationized dextran hydrochloride being soluble in water, ethanol and acetone and having a quaternary nitrogen substitution degree of 17.1%, a hydroxypropyl substitution degree of 70%, an intrinsic viscosity of 0.13 (n=31.2) and a specific rotation of +83°.

EXAMPLE 16

Example 14 was repeated except that 81 g of dextran having an average molecular weight of about 59,000 and 150 ml of water were used. There was obtained 165 g of a white powder of cationized devtran hydrochloride being soluble in water, ethanol and acetone and having a quaternary nitrogen substitution degree of 16.2%, a hydroxypropyl substitution degree of 67%, an intrinsic viscosity of 0.31 (n=181) and a specific rotation of +88°.

EXAMPLE 17

Example 14 was repeated except that 81 g of dextran having an average molecular weight of about 664,000 and 300 ml of water were used. There was obtained 160 g of a white powder of purified cationized dextran hydrochloride being soluble in water, ethanol and acetone and having a quaternary nitrogen substitution degree of 13.4%, a hydroxypropyl substitution degree of 64%, an intrinsic viscosity of 0.71 (n=2048) and a specific rotation of +90°.

EXAMPLE 18

Example 14 was repeated except that 81 g of dextran having an average molecular weight of about 1,660,000 and 500 ml of water were used. There was obtained 145 g of a white powder of pure cationized dextran hydrochloride being soluble in water and ethanol and having a quaternary nitrogen substitution degree of 11.8%, a hydroxypropyl substitution degree of 52%, an intrinsic viscosity of 1.60 (n=5122) and a specific rotation of +105°.

EXAMPLE 19

81 g of dextran having an average molecular weight of about 37,000 and 300 ml of water were charged. Then, 5 ml of a 40% by weight aqueous solution of sodium hydroxide was added. The mixture was stirred for 10 minutes and 180 ml of an aqueous solution containing 76 g of glycidyl trimethyl ammonium chloride was added. The mixture was heated to 60° C. and reacted for 5 hours. Ethylene oxide (132 g) was added, and the mixture was heated to 50° C. and reacted for 3 hours. The reaction mixture was neutralized with acetic acid, and dialyzed against flowing water for 24 hours. The dialyzate was lyophilized to give 130 g of a white powder of cationized dextran hydrochloride being soluble in water and ethanol and having a quaternary nitrogen substitution degree of 9.1%, a hydroxyethyl substitution degree of 64%, an intrinsic viscosity of 0.20 ($n=113$) and a specific rotation of $+115°$.

EXAMPLE 20

81 g of dextran having an average polymerization of about 59,000 and 200 ml of water were charged. Then, 25 ml of a 40% by weight aqueous solution of sodium hydroxide was added, and the mixture was stirred for 10 minutes. Then, 1200 ml of an aqueous solution containing 389 g of glycidyl triethyl ammonium chloride was added. The mixture was worked up in the same way as in Example 19 to give 170 g of a white powder of cationized dextran hydrochloride being soluble in water, ethanol and acetate and having a quaternary nitrogen substitution degree of 20.0%, a hydroxyethyl substitution degree of 48%, an intrinsic viscosity of 0.38 ($n=181$) and a specific rotation of $+85°$.

EXAMPLE 21

81 g of dextran having an average molecular weight of about 37,000 and 150 ml of water. Then, 10 ml of a 40% by weight aqueous solution of sodium hydroxide was added, and the mixture was stirred for 10 minutes. Ethylene oxide (88 g) was added, and the mixture was heated to 50° C. and reacted for 3 hours. Then, 360 ml of an aqueous solution containing 152 g of glycidyl trimethyl ammonium chloride was added. The mixture was heated to 50° C. and reacted for 5 hours. The reaction mixture was neutralized with hydrochloric acid, and dialyzed against flowing water for 24 hours. The dialyzate was lyophilized to give 160 g of a white powder of cationized dextran hydrochloride being soluble in water and ethanol and having a quaternary nitrogen substitution degree of 11.2%, a hydroxyethyl substitution degree of 53%, an intrinsic viscosity of 0.23 ($n=113$) and a specific rotation of $+110°$.

EXAMPLE 22

Example 21 was repeated except that 116 g of propylene oxide was used instead of the ethylene oxide. There was obtained 160 g of a white powder of cationized dextran hydrochloride being soluble in water and ethanol and having a quaternary nitrogen substitution degree of 10.7%, a hydroxypropyl substitution degree of 58%, an intrinsic viscosity of 0.22 ($n=113$) and a specific rotation of $+100°$.

EXAMPLE 23

Example 22 was repeated except that 150 ml of an aqueous solution containing 115 g of 3-chloro-2-hydroxypropyltriethyl ammonium chloride was used. There was obtained 145 g of a white powder of cationized dextran hydrochloride being soluble in water and ethanol and having a quaternary nitrogen substitution degree of 6.3%, a hydroxypropyl substitution degree of 61%, an intrinsic viscosity of 0.25 ($n=113$) and a specific rotation of $+105°$.

EXAMPLE 24

81 g of dextran having an average molecular weight of about 10,450 and 100 ml of water were charged. Then, 165 ml of a 40% by weight aqueous solution of sodium hydroxide, 180 ml of an aqueous solution containing 76 g of glycidyl trimethyl ammonium chloride and 120 g of ethylene chlorohydrin were added with stirring. The mixture was heated to 60° C. and reacted for 3 hours. The reaction mixture was neutralized with hydrochloric acid, and dialyzed against flowing water for 24 hours. The dialyzate was lyophilized to give 110 g of a white powder of cationized dextran hydrochloride having a quaternary nitrogen substitution degree of 8.3%, a hydroxyethyl substitution degree of 37%, an intrinsic viscosity of 0.11 ($n=31.2$) and a specific rotation of $+130°$.

EXAMPLE 25

81 g of dextran having an average molecular weight of about 664,000 and 1000 ml of water were charged. Then, 110 ml of a 40% by weight aqueous solution of sodium hydroxide was added, and the mixture was stirred for 10 minutes. Further, 80 g of ethylene chlorohydrin was added, and the mixture was heated to 60° C. and reacted for 3 hours. 300 ml of an aqueous solution containing 97 g of glycidyl triethyl ammonium chloride was added, and the mixture was reacted at 50° C. for 5 hours. The reaction mixture was neutralized with hydrochloric acid, and precipitated three times with acetone from water and ethanol. The precipitates were dried in vacuum at 50° C. to give 90 g of cationized dextran hydrochloride having a quaternary nitrogen substitution degree of 4.8%, a hydroxyethyl substitution degree of 19%, an intrinsic viscosity of 0.68 ($n=2048$) and a specific rotation of $+150°$.

EXAMPLE 26

Example 16 was repeated except that 300 ml of an aqueous solution containing 230 g of 3-chloro-2-hydroxypropyl triethyl ammonium chloride was used. There was obtained 170 g of a white powder of cationized dextran hydrochloride being soluble in water, ethanol and acetone and having a quaternary nitrogen substitution degree of 13.0%, a hydroxypropyl substitution degree of 70%, an intrinsic viscosity of 0.33 ($n=181$) and a specific rotation $+85°$.

FORMULATION EXAMPLE 10

Shampoos having the compositions (A) to (G) shown in Table 5 were prepared by using the cationized dextran derivatives obtained in the above Examples. As a comparison, a shampoo not containing a cationized dextran derivative was prepared. The properties of the shampoos, such as smoothness during use, hair creaking during rinsing, and the softness and gloss of hair on finishing, were tested, and the results are shown in Table 5. The standards of evaluation were the same as in Formulation Example 1.

The results given in Table 5 demonstrate that the shampoos containing the cationized dextran derivatives give better feel to hair during use, rinsing and finishing than the shampoo not containing the cationized dextran. hair on finishing than the hair rinse not containing the cationized dextran derivative.

TABLE 5

Recipe Amount (% by weight)

| Component | (A) | (B) | (C) | (D) | (E) | (F) | (G) | Comparison |
|---|---|---|---|---|---|---|---|---|
| Polyoxyethylene lauryl ether sulfate sodium salt ($\overline{p} = 3$) | 7.5 | 7.5 | 7.5 | 7.5 | 7.5 | 7.5 | 7.5 | 7.5 |
| 2-Lauryl-N—carboxymethyl-N—hydroxyethyl imidazolium betaine | 10 | 10 | 10 | 10 | 10 | 10 | 10 | 10 |
| Coconut oil fatty acid diethanolamide | 3 | 3 | 3 | 3 | 3 | 3 | 3 | 3 |
| Cationized dextran (Example No.) | 15 | 16 | 17 | 19 | 20 | 22 | 24 | — |
| Amount of the cationized dextran | 0.5 | 0.5 | 0.5 | 1.0 | 0.2 | 0.5 | 0.5 | 0 |
| Perfume, coloring agent, antiseptic | suitable amount | suitable amount | suitable amount | suitable amount | suitable amount | suitable amount | suitable amount | suitable amount |
| Purified water | balance | balance | balance | balance | balance | balance | balance | balance |
| Smoothness during use | O | O | O | O | O | O | O | Δ |
| Hair creaking during rinsing | O | O | O | O | O | O | O | X |
| Softness of hair on finishing | O | O | O | O | O | O | O | X |
| Ease of grooming on finishing | O | O | O | O | O | O | O | X |
| Gloss of hair on finishing | O | O | O | O | O | O | O | Δ |
| Ease of combing on finishing | O | O | O | O | O | O | O | X |

TABLE 6

Recipe Amount (% by weight)

| Component | (A) | (B) | (C) | (D) | (E) | (F) | Comparison |
|---|---|---|---|---|---|---|---|
| Distearyldimethyl ammonium chloride | 5 | 5 | 5 | 5 | 5 | 5 | 5 |
| Cetyl alcohol | 3 | 3 | 3 | 3 | 3 | 3 | 3 |
| Propylene glycol | 6 | 6 | 6 | 6 | 6 | 6 | 6 |
| Polyoxyethyleneoleyl alcohol | 1 | 1 | 1 | 1 | 1 | 1 | 1 |
| 2-Hexyldecanol | 1 | 1 | 1 | 1 | 1 | 1 | 1 |
| Cationized dextran (Example No.) | 14 | 16 | 21 | 22 | 23 | 25 | — |
| Amount of the cationized dextran | 1 | 1 | 1 | 1 | 2 | 3 | 0 |
| Perfume, coloring agent, antiseptic | suitable amount | suitable amount | suitable amount | suitable amount | suitable amount | suitable amount | suitable amount |
| Purified water | balance | balance | balance | balance | balance | balance | balance |
| Softness of hair on finishing | O | O | O | O | O | O | Δ |
| Ease of grooming on finishing | O | O | O | O | O | O | Δ |
| Gloss of hair on finishing | O | O | O | O | O | O | Δ |
| Ease of combing on finishing | O | O | O | O | O | O | X |

FORMULATION EXAMPLE 11

Hair rinses having the compositions (A) to (F) shown in Table 6 were prepared by using the cationized dextran derivatives prepared in the above Examples. As a comparison, a hair rinse not containing a cationized dextran derivative was prepared. The properties of the hair rinses, such as the softness and gloss of hair on finishing, were tested and the results are shown in Table 6. The standards of evaluation were the same as in Formulation Example 1.

It is seen from Table 6 that the hair rinses containing the cationized dextran derivatives give better feel to

FORMULATION EXAMPLE 12

Hair treating agents having the compositions (A) to (D) shown in Table 7 were prepared by using the cationized dextran derivatives obtained in the above Examples. As a comparison, a hair treating agent not containing a cationized dextran derivative was prepared. The properties of the hair treating agents, such as the softness, ease of grooming, gloss and ease of combing of the hair after use, were tested, and the results are shown in Table 7. The standards of evaluation were the same as in Formulation Example 1.

The results given in Table 7 show that the hair treating agents containing the cationized dextran derivatives give better feel to hair after use than the hair treating agent not containing the cationized dextran derivative.

TABLE 7

| | Recipe Amount (% by weight) | | | | |
|---|---|---|---|---|---|
| Component | (A) | (B) | (C) | (D) | Comparison |
| Liquid lanolin | 1.5 | 1.5 | 1.5 | 1.5 | 1.5 |
| Cetanol | 7.5 | 7.5 | 7.5 | 7.5 | 7.5 |
| 2-Hexyldecanol | 9 | 9 | 9 | 9 | 9 |
| Polyoxyethylene-oleyl ether | 6 | 6 | 6 | 6 | 6 |
| Stearyl dimethyl ammonium chloride | 6 | 6 | 6 | 6 | 6 |
| Glycerol | 3 | 3 | 3 | 3 | 3 |
| Cationized dextran (Example No.) | 16 | 18 | 23 | 26 | — |
| Amount of the cationized dextran | 1 | 1 | 2 | 0.5 | 0 |
| Perfume, coloring agent, antiseptic | suitable amount | suitable amount | suitable amount | suitable amount | suitable amount |
| purified water | balance | balance | balance | balance | balance |
| Softness of hair after use | O | O | O | O | Δ |
| Ease of grooming after use | O | O | O | O | Δ |
| Gloss of hair after use | O | O | O | O | Δ |
| Ease of combing after use | O | O | O | O | Δ |

FORMULATION EXAMPLE 13

Hair tonics having the compositions (A) and (B) shown in Table 8 were prepared by using the cationized dextran derivatives obtained in the above Examples. As a comparison, a hair tonic not containing a cationized dextran derivative was prepared. The properties of the hair tonics, such as the gloss, ease of grooming and ease of combing of hair, were tested, and the results are shown in Table 8. The standards of evaluation were the same as in Formulation Example 1.

TABLE 8

| | Recipe Amount (% by weight) | | |
|---|---|---|---|
| Compound | (A) | (B) | Comparison |
| Modified ethanol (95%) | 60 | 60 | 60 |
| Menthol | 0.2 | 0.2 | 0.2 |
| Castor oil | 2 | 2 | 2 |
| Polyoxyethylene lauryl ether sodium phosphate | 2 | 2 | 2 |
| Salicylic acid | 0.1 | 0.1 | 0.1 |
| Cationized dextran (Example No.) | 16 | 19 | — |
| Amount of the cationized dextran | 1 | 1 | 0 |
| Perfume | suitable amount | suitable amount | suitable amount |
| Purified water | balance | balance | balance |
| Ease of hair grooming after use | O | O | X |
| Gloss of hair after use | O | O | X |
| Ease of combing after use | O | O | Δ |

FORMULATION EXAMPLE 14

An aerosol lacquer of the following formulation was prepared by using the cationized dextran derivative obtained in Example 14.

| Component | Amount (% by weight) |
|---|---|
| Cationized dextran | 3 |
| Perfume | 0.2 |
| Ethanol | balance |

Trichloromonofluoromethane (47 g) and 28 g of dichlorodifluoromethane were added to 25 g of the above solution to form an aerosol lacquer in a container.

When the aerosol lacquer was sprayed onto the hair, good combability was obtained with good gloss and soft feel.

FORMULATION EXAMPLE 15

A hairdressing lotion of the following was prepared by using the cationized dextran derivative obtained in Example 19.

| Component | Amount (% by weight) |
|---|---|
| Ethanol | 50 |
| Perfume, dye | suitable amounts |
| Cationized dextran | 3 |
| Purified water | balance |

When this lotion was applied to the hair in a usual manner, good combability was obtained with gloss. These properties lasted for an extended period of time.

FORMULATION EXAMPLE 16

In accordance with the following formulation, the cationized dextran derivative obtained in Example 15 was combined with an imidazoline-type amphoteric surfactant to form a double salt. The double salt was uniformly dissolved in a mixed solvent of ethanol and water to prepare a dispenser-type hair conditioner.

| Component | Amount (% by weight) |
|---|---|
| Cationized dextran | 0.5 |
| Imidazoline-type amphoteric surfactant (2-alkyl-N—carboxymethyl-N—hydroxy-ethylimidazolium betaine) | 0.5 |
| Ethanol/water (80/20) | 99 |

When the hair conditioner was applied to the hair in a usual manner, good combability was obtained with good gloss and wet feeling.

FORMULATION EXAMPLE 17

A cleansing cream having the following formulation was prepared by using the cationized dextran derivative obtained in Example 23.

| Component | Amount (% by weight) |
|---|---|
| Liquid paraffin | 40 |
| Solid paraffin | 10 |
| Vaseline | 15 |
| Beeswax | 3 |
| Sorbitan sesquioleate | 4 |
| Polyoxyethylene sorbitan monooleate | 1 |

-continued

| Component | Amount (% by weight) |
|---|---|
| Perfume, antioxidant, antiseptic | suitable amount |
| Cationized dextran | 1.5 |
| Purified water | balance |

This cream had better spreadability and oily feeling than a cream not containing the cationized dextran.

FORMULATION EXAMPLE 18

A neutral cream having the following formulation was prepared by using the cationized dextran derivative obtained in Example 26.

| Component | Amount (% by weight) |
|---|---|
| Liquid paraffin | 10 |
| Vaseline | 10 |
| Glycerin monostearate | 0.5 |
| Isopropyl palmitate | 2 |
| Glycerol | 3 |
| Perfume, antioxidant, antiseptic | suitable amount |
| Cationized dextran | 1 |
| Purified water | balance |

This cream had better smoothness and wet feeling than a cream not containing the cationized dextran.

FIG. 1-B shows the mutual action of a cationized polysaccharide and an imidazoline-type amphoteric surfactant (SOFTAZOLINE CL, a tradename for a product of Kawaken Fine Chemical Co., Ltd.), which was measured under the following conditions.

MEASURING CONDITIONS

A 5% solution of SOFTAZOLINE CL was added to a 0.1% solution of the cationized polysaccharide, and the amount of the precipitated double salt was measured.

Figure 6:
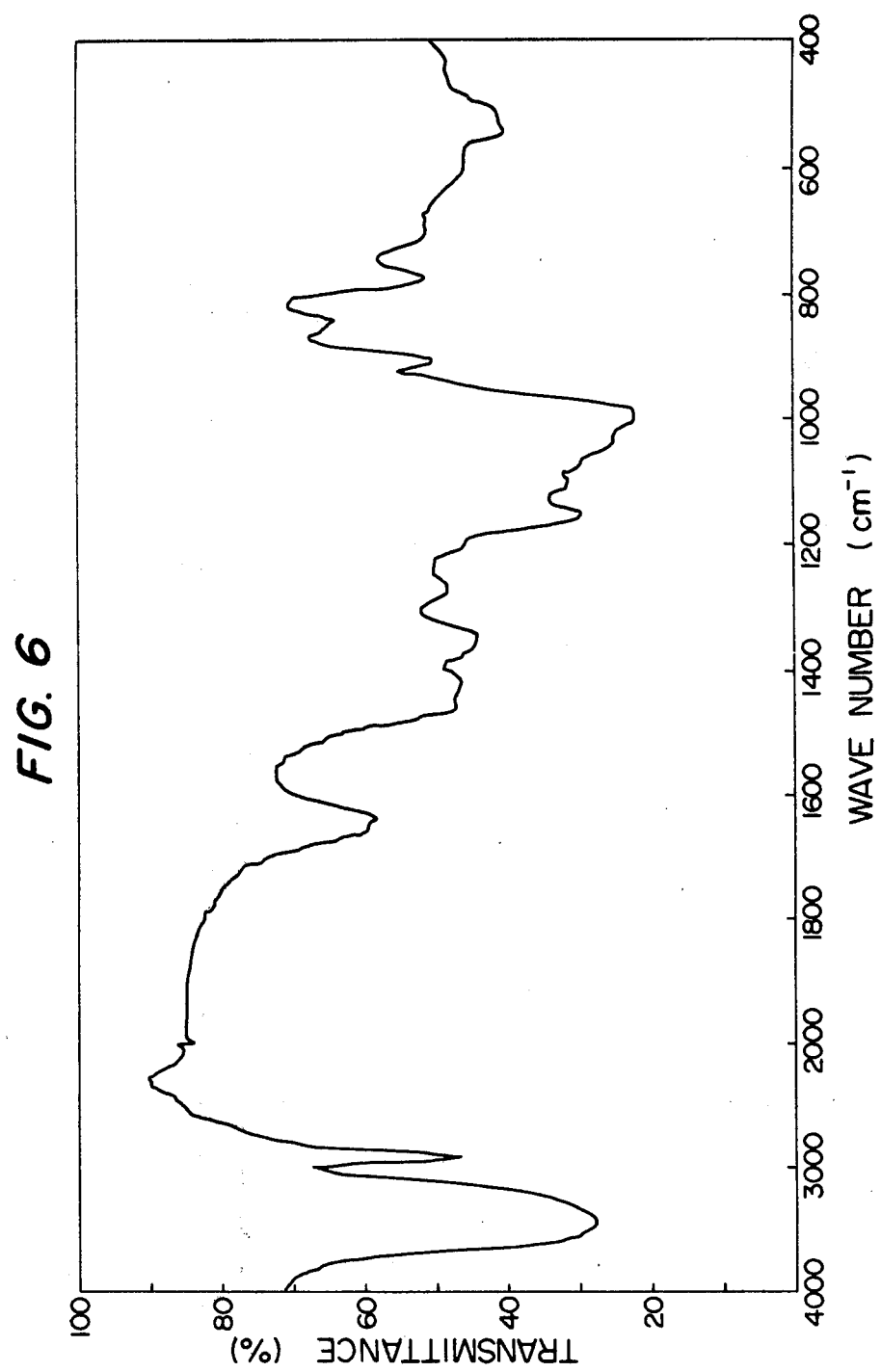
FIG. 6 is an infrared absorption spectral chart of the starting dextran used in Example 21.

FIG. 6 is an infrared absorption spectral chart of the starting dextran used in Example 21.

| | |
|---|---|
| 3800–3200 cm$^{-1}$: | —OH |
| 1200–1050 cm$^{-1}$: | —CO |
| 910, 840, 770 cm$^{-1}$: | α-1,6' linkage |

Figure 7:
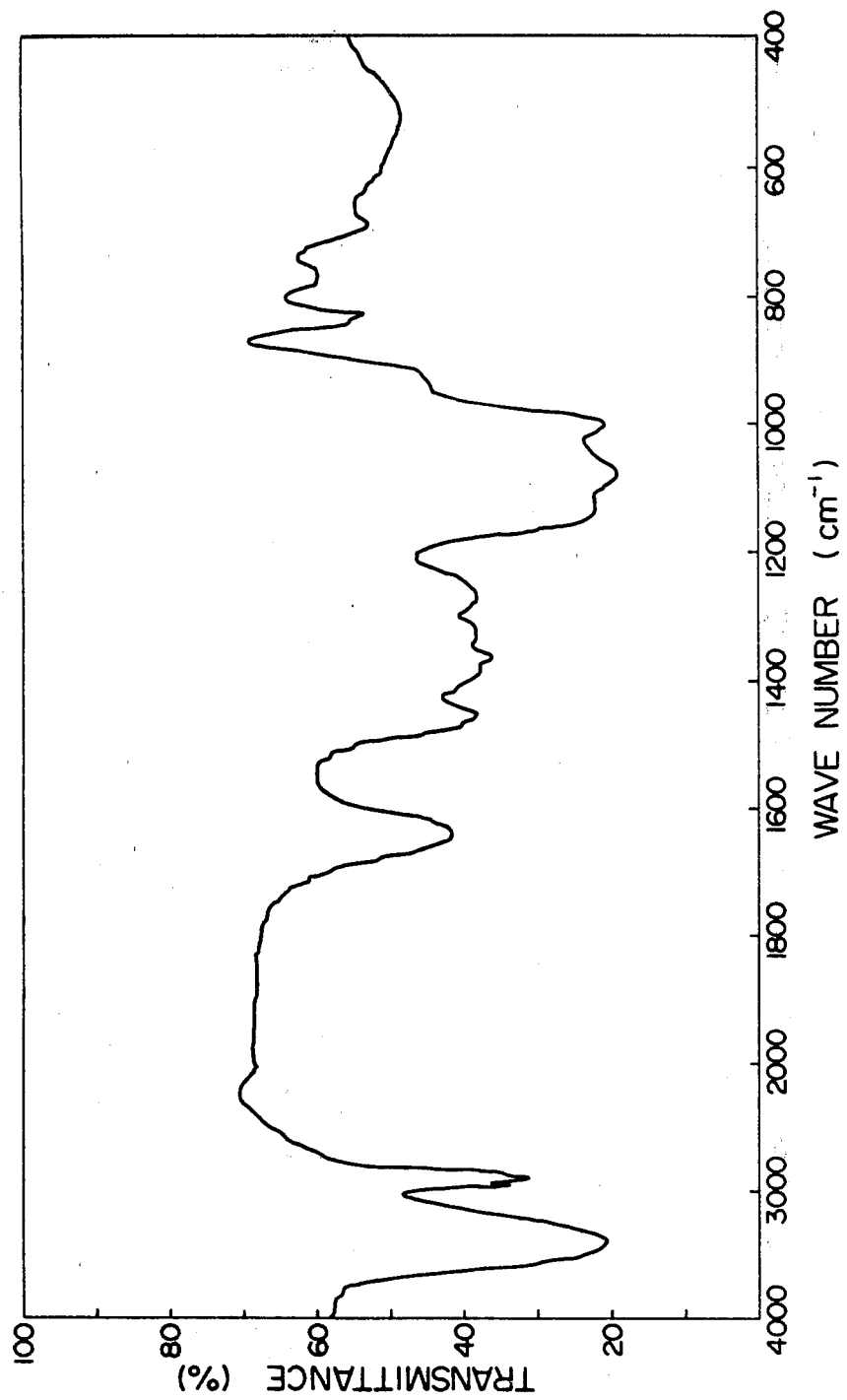
FIG. 7 is an infrared absorption spectral chart of the cationized dextran hydrochloride obtained in Example 21.

FIG. 7 is an infrared absorption spectral chart of the cationized dextran hydrochloride obtained in Example 21.

| | |
|---|---|
| 2950–2750 cm$^{-1}$: | —CH$_2$— |
| 1460 cm$^{-1}$: | —CH$_3$— |
| 910, 840, 770 cm$^{-1}$: | α1,6' linkage |

Figure 8:
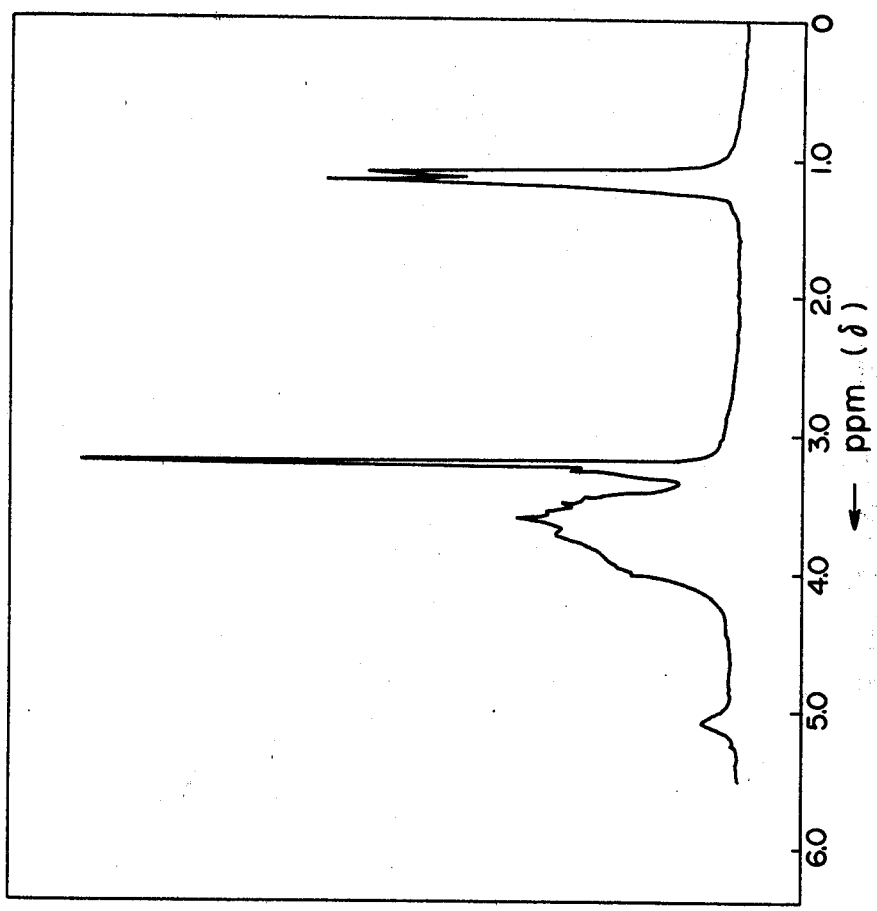
FIG. 8 is a nuclear magnetic resonance spectral chart of the cationized dextran hydrochloride obtained in Example 16.

FIG. 8 is a nuclear magnetic resonance spectral chart of the cationized dextran hydrochloride obtained in Example 16.

δ1.0–1.3: —C—CH$_3$

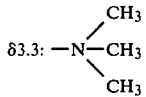

δ3.3–4.2: glucose ring

EXAMPLE 27

105 g of dextran having an average molecular weight of about 34,000 was dissolved in 125 ml of water. Then, 40 ml of a 48.5% by weight aqueous solution of sodium hydroxide and 190 ml of an aqueous solution containing 110 g of 3-chloro-2-hydroxypropyltrimethyl ammonium chloride were added. The mixture was heated to 60° C., and reacted for 3 hours. The reaction mixture was neutralized with hydrochloric acid, and precipitated four times with acetone from water. The precipitates were spray-dried to give 140 g of a white powder of pure cationized dextran hydrochloride being soluble in water and 60% ethanol and having a quaternary nitrogen substitution degree of 14.0%, an intrinsic viscosity of 0.180 (n=104) and a specific rotating of +150°.

EXAMPLE 28

200 g of dextran having an average molecular weight of about 664,000 was dissolved in 660 ml of an aqueous solution containing 240 g of 3-chloro-2-hydroxypropyltrimethyl ammonium chloride. Then, 65 ml of a 48.5% by weight aqueous solution of sodium hydroxide was added. The mixture was heated to 60° C. and reacted for 5 hours. The reaction mixture was neutralized with hydrochloric acid, and worked up in the same way as in Example 27 to give 280 g of a white powder of pure cationized dextran hydrochloride having a quaternary nitrogen substitution degree of 15.5%, an intrinsic viscosity of 0.79 (n=2048) and a specific rotation of +141°.

EXAMPLE 29

105 g of dextran having an average molecular weight of about 34,000 was dissolved in 125 ml of water, and then 40 ml of a 48.5% by weight aqueous solution of sodium hydroxide and 190 ml of an aqueous solution containing 110 g of 3-chloro-2-hydroxypropyltrimethyl ammonium chloride were added. The mixture was heated to 60° C. and reacted for 3 hours. Then, 150 g of propylene oxide was added. In a closed atmosphere, the mixture was heated to 50° C. and reacted for 6 hours. The reaction mixture was neutralized with hydrochloric acid and worked up in the same way as in Example 14 to give 140 g of a powder of pure cationized dextran hydrochloride having a quaternary nitrogen substitution degree of 12.3%, a hydroxypropyl substitution degree of 60%, an intrinsic viscosity of 0.170 (n=104) and a specific rotation of +102°.

EXAMPLE 30

200 g of dextran having an average molecular weight of about 664,000 was dissolved in 660 ml of an aqueous solution containing 240 g of 3-chloro-2-hydroxypropyltrimethyl ammonium chloride. Then, 65 ml of a 48.5% by weight aqueous solution of sodium hydroxide was added. The mixture was heated to 60° C. and reacted for 5 hours. Ethylene oxide (270 g) was added, and in a closed atmosphere, the mixture was heated to 50° C. and reacted for 5 hours. The reaction mixture was neutralized with hydrochloric acid and worked up in the same way as in Example 14 to give 400 g of a white powder of pure cationized dextran hydrochloride having a quaternary nitrogen substitution degree of 14.3%, a hydroxyethyl substitution degree of 71%, an intrinsic viscosity of 0.81 (n=2048) and a specific rotation of +94°.

EXAMPLE 31

105 g of dextran having an average molecular weight of 34,000 was dissolved in 250 ml of an aqueous solution containing 110 g of 3-chloro-2-hydroxypropyltrimethyl ammonium chloride. Then, 40 ml of a 48.5% by weight aqueous solution of sodium hydroxide was added, and the mixture was heated to 60° C. and reacted for 3 hours. Then, 190 g of butylene oxide was added, and in a closed atmosphere, the mixture was heated to 60° C. and reacted for 12 hours. The reaction mixture was neutralized with hydrochloric acid, and worked up in the same way as in Example 14 to give 224 g of a powder of pure cationized dextran hydrochloride having a quaternary nitrogen substitution degree of 14.5%, a hydroxybutyl substitution degree of 57%, an intrinsic viscosity of 0.182 (n=104), and a specific rotation of +98°.

What we claim is:

1. A cationized dextran of the following formula

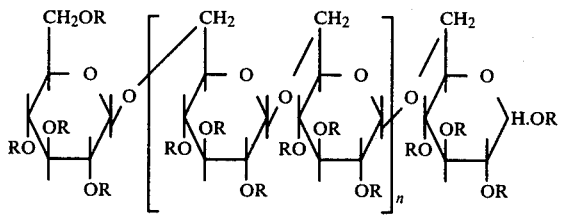

wherein R represents a group selected from the class consisting of a hydrogen atom, hydroxy lower alkyl groups, and quaternary nitrogen-containing groups of the formula

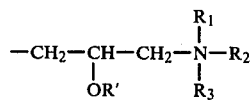

in which $R_1$, $R_2$ and $R_3$ each represent a lower alkyl group, and R' represents a hydrogen atom or a hydroxy lower alkyl group, and n is a positive number of from 1 to 8,000; two or more R groups may be identical or different provided that at least one of R groups is the quaternary nitrogen-containing group of the above formula;

and a salt thereof.

2. The compound of claim 1 wherein the hydroxy lower alkyl group represented by R and R' is a hydroxy($C_1$-$C_4$ alkyl) group, and the lower alkyl group represented by $R_1$, $R_2$ and $R_3$ is a $C_1$-$C_4$ alkyl group.

3. The cationized dextran of claim 1 or 2 having a substitution degree of about 3 to about 100%.

4. The cationized dextran of claim 1 or 2 having a substitution degree of about 5 to about 95%.

5. The cationized dextran of claim 1 or 2 wherein n is a positive number of 4 to 6,000.

6. A hair or skin cosmetic composition comprising (1) a hair or skin cosmetic base and (2) a cationized dextran of the formula

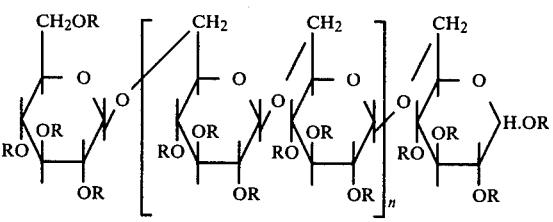

wherein R represents a group selected from the class consisting of a hydrogen atom, hydroxy lower alkyl groups, and quaternary nitrogen-containing groups of the formula

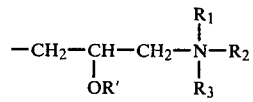

in which $R_1$, $R_2$ and $R_3$ each represent a lower alkyl group, and R' represents a hydrogen atom or a hydroxy lower alkyl group, and n is a positive number of from 1 to 8,000; two or more R groups may be identical or different provided that at a least one of R groups is the quaternary nitrogen-containing group of the above formula;

or its salt acceptable for hair or skin cosmetics.

7. The cosmetic composition of claim 6 which comprises from about 0.1 to about 5% by weight of the cationized dextran.

8. The cosmetic composition of claim 6 or 7 wherein the cationized dextran has a quaternary nitrogen substitution degree of about 3 to about 40%, a hydroxy lower alkyl group substitution degree of 0 to about 90%, with the total substitution degree being about 5 to about 95%, and n is a positive number of about 4 to about 6,000.

* * * * *